United States Patent [19]
Scarborough et al.

[11] Patent Number: 6,162,258
[45] Date of Patent: Dec. 19, 2000

[54] LYOPHILIZED MONOLITHIC BONE IMPLANT AND METHOD FOR TREATING BONE

[75] Inventors: Nelson L. Scarborough, Ocean; Todd M. Boyce, Aberdeen, both of N.J.

[73] Assignee: Osteotech, Inc., Eatontown, N.J.

[21] Appl. No.: 09/382,331

[22] Filed: Aug. 25, 1999

[51] Int. Cl.$^7$ ...................................... A61F 2/36
[52] U.S. Cl. ........................................ 623/23.63
[58] Field of Search ............................. 623/11.11, 16.11, 623/23.51, 23.63, 23.76

[56] References Cited

U.S. PATENT DOCUMENTS

| | | | |
|---|---|---|---|
| 5,236,456 | 8/1993 | O'Leary et al. | 623/16 |
| 5,507,813 | 4/1996 | Dowd et al. | |
| 5,861,438 | 1/1999 | MacLean et al. | 514/648 |

OTHER PUBLICATIONS

Boyne, P., Cryobiology, vol. 4, No. 6 (1968), pp. 341–357.
Pappas, A., Cryobiology, vol. 4, No. 6 (1968), pp. 358–375.
Triantafyllou et al., Acta Orthopaedica Belgica, vol. 41, Suppl. I, (1975), pp. 35–44.
Pelker, et al., Clinical Orthopaedics and Related Research, No. 174, (Apr. 1983), pp. 54–57.
Pelker et al., Journal of Orthopaedic Research, vol. 1, No. 4, (1984), pp. 405–411.
Pelker et al., Orthopedic Clinics of North America, vol. 18, No. 2, (Apr. 1987), pp. 235–239.
Jerosch et al., Zeitschrift Orthopädie 132, (1994), pp. 335–341.
Voggenreiter et al., Archives of Orthopaedic and Traumatic Surgery, vol. 113,(1994),pp. 294–296.
Kang et al., Yonsei Medical Journal, vol. 36, No. 4, (1995), pp. 332–335.
Bianchi et al., 21$^{st}$ Annual Meeting, American Association of Tissue Banks,(Aug. 23–27, 1997), p. 48.
Balderson et al., 45$^{th}$ Annual Meeting, Orthopaedic Research Society,(Feb. 1–4, 1999), p. 785.

*Primary Examiner*—Jeffrey A. Smith
*Assistant Examiner*—Eduardo C. Robert
*Attorney, Agent, or Firm*—Dilworth & Barrese, LLP

[57] ABSTRACT

Monolithic bone intended for implantation is treated in order to conserve its mechanical strength during lyophilization and subsequent packaging and to maintain the strength of the bone during the storage period preceding the rehydration and implantation of the bone. The method of treatment comprises contacting the bone with a mechanical strength-conserving amount of at least one biocompatible mechanical strength-conserving agent, the agent being a liquid organic material which is capable of penetrating and remaining in the bone during its lyophilization, packaging and storage, lyophilizing the bone containing the mechanical strength-conserving agent and packaging the lyophilized bone.

40 Claims, No Drawings

LYOPHILIZED MONOLITHIC BONE IMPLANT AND METHOD FOR TREATING BONE

BACKGROUND OF THE INVENTION

Monolithic bone intended for implantation is treated in order to conserve its mechanical strength during lyophilization and subsequent packaging and to maintain the strength of the bone during the storage period preceding the rehydration and implantation of the bone.

The use of preserved bone intended for implantation to replace diseased or missing parts is common. The successful application of such bone is predicated on sound knowledge of its biologic properties and its capacity to withstand the stresses to which it will be subjected. When mineralized bone is used in grafts, it is primarily because of its inherent strength, i.e., its load bearing ability at the recipient site. The biomechanical properties of bone grafts upon implantation are determined by many factors, including the specific site from which the bone is taken; the age, sex, and physical characteristics of the donor; and the method chosen to prepare, preserve, and store the bone prior to implantation. A more detailed explanation of the alteration of the biomechanical properties of bone by the methods chosen for its preservation and storage may be found in Pelker et al., *Clin. Orthop. Rel. Res.*, 174:54–57(1983). However, the needs for processing (e.g., to preserve the graft for later use and to remove immunogenic cellular materials) can conflict with the need to conserve the mechanical strength of the bone. During the preparation of bone intended for implantation the porous matrix is typically contacted with one or more treatment fluids to variously clean, defat, sterilize, virally inactivate, disinfect, and/or demineralize the bone or to impregnate the bone with one or more pharmacological agents (antibiotics, bone growth factors, etc.) so the bone can act as a drug delivery system. See U.S. Pat. No. 5,846,484 for a detailed explanation of the treatment of bone intended for implantation. Some treatment processes, such as irradiation and lyophilization, can work against conservation of the mechanical strength of bone and can lessen the bones weight bearing properties.

It is generally accepted that freezing monolithic bone to temperatures as cold as −70° C. prior to its packaging and storage results in little if any alteration in its physical properties. However, freezing bone as a preservation technique is costly and can be logistically difficult, e.g., shipping and storage. Lyophilization (freeze-drying) is commonly performed on bone to permit its shelf storage for up to several years without spoilage. Lyophilization removes excess moisture from the bone and reduces its antigenicity. According to The American Association of Tissue Banks, lyophilized whole bone containing no more than 6% moisture can be stored at ambient temperatures for up to five years after processing. However, adverse changes in the biomechanical properties of the bone have been found to result from the lyophilization procedure. Lyophilization can result in damage to the bone due to dimensional changes that occur during the freezing and drying operations. The adverse mechanical changes appear to be associated with damage occurring in the bone matrix, specifically, ultrastructural cracks along the collagen fibers. These effects appear to be magnified when lyophilization and gamma irradiation are used together. Studies using rat bones to model the effects of lyophilization upon the compressive properties of cancellous bone (compression strength of tail vertebrae) and the bending and torsional properties of the long bones indicate that compressive strength can be reduced by up to 30% with little or no change in stiffness, bending strength can be reduced by as much as 40%, and torsional strength can be reduced by up to 60%. These changes have been found to occur even after the bone has been rehydrated. A more detailed explanation of the effects of lyophilization on mineralized bone can be found in Kang et al., *Yonsei Med J* 36:332–335(1995), and Pelker et al., *J. Orthop. Res.* 1:405–411(1984). Because freezing and thawing bone is minimally damaging to the bone, whereas lyophilization results in reduction in the mechanical strength of the bone, it is the inventors' belief that the mechanical strength-conserving agent is not acting as a cryopreservative (i.e., minimizing crystal growth during freezing) but rather in some new, not entirely understood, manner to diminish the dimensional changes associated with lyophilization.

Thus, it is desirable to provide a method for treating bone which is to undergo lyophilization as a prelude to its packaging and storage that will better conserve the biomechanical properties of the bone, i.e., its mechanical strength, as compared to untreated lyophilized bone, from the time the bone is harvested through the packaging and storage operations and to time of implantation.

SUMMARY OF THE INVENTION

It is therefore an object of the present invention to provide a method for treating monolithic bone intended for implantation in order to conserve the mechanical strength of the bone during its lyophilization and subsequent packaging and storage and to substantially maintain such strength until the bone is rehydrated and implanted.

It is a further object of the invention to provide a treatment with minimal negative impact to the biological properties of the bone graft.

It is a further object of the invention to provide a treatment that acts as an antimicrobial/preservative agent.

It is a further object of the invention to provide a method for packaging lyophilized monolithic bone so that the bone may be stored at ambient temperatures for an extended period of time, e.g., up to five years without excessive loss of its mechanical strength.

It is a further object of the invention to provide a method for the rehydration of lyophilized monolithic bone such that the mechanical strength of the bone at the time of its implantation is optimized.

It is a further object of the invention to provide a method that decreases the time necessary to rehydrate a lyophilized bone intended for implantation.

It is a further object of the invention to provide a method that minimizes the tendency for a partially rehydrated lyophilized graft to fracture due to the insertion forces applied by the surgeon.

It is a further object of the invention to provide a lyophilized monolithic bone implant containing a mechanical strength-conserving agent and, optionally, one or more medically/surgically substances, e.g., an osteogenic material such as bone morphogenic proteins (BMPs).

In keeping with these and related objectives of the invention, there is provided a method for treating monolithic bone intended for implantation to conserve the mechanical strength of the bone during lyophilization and subsequent packaging and to maintain such strength during the storage of the bone preceding its implantation. The method comprises:

a) contacting the bone with a mechanical strength-conserving amount of at least one biocompatible mechanical strength-conserving agent, said agent being a liquid organic material or solution, mixture, or suspension thereof, which is capable of penetrating and remaining in the bone during its lyophilization, packaging and storage;

b) lyophilizing the bone containing the mechanical strength-conserving agent; and, c) packaging the lyophilized bone.

The invention further includes the lyophilized bone obtained by the foregoing method, the implantable bone obtained following rehydration of the lyophilized bone and, more generally, any lyophilized bone containing a mechanical strength-conserving agent as disclosed herein.

The expression "monolithic bone" as utilized herein refers to relatively large pieces of human or animal bone, i.e., pieces of bone, autograft, allograft or xenograft, that are of such size as to be capable of withstanding the sort of mechanical loads to which functioning bone is characteristically subjected. The monolithic bone of this invention is to be distinguished from particles, filaments, threads, etc. as disclosed in U.S. Pat. Nos. 5,073,373, 5,314,476 and 5,507,813, which, due to their relatively small dimensions, are incapable of sustaining significant mechanical loads, either individually or in the aggregate. It is further to be understood that the expression "monolithic bone" refers to fully mineralized bone, i.e., bone with its full natural level of mineral content, and to such bone that has been demineralized to some minor extent, i.e., to an extent which reduces the original mechanical strength of the bone by no more than about 50 percent. The monolithic bone can be provided as a single integral piece of bone or as a piece of bone permanently assembled from a number of smaller bone elements, e.g., as disclosed and claimed in U.S. Pat. No. 5,899,939 the contents of which are incorporated herein by reference. Although monolithic bone can contain factors which are osteogenic, monolithic bone can also contain additional materials, e.g., as disclosed in U.S. Pat. No. 5,290,558 the contents of which are incorporated herein by reference, which will remain with the bone after its rehydration and will be present at the time of implantation.

The expression "mechanical strength" as utilized herein is intended to mean any one of the principal biomechanical properties of bone, specifically including compression strength, flexural modulus, and torsional modulus, as well as the sum of these properties, that are characteristic of bone.

The expression "conserving the mechanical strength of the bone" and expressions of like import shall be understood herein to mean that the monolithic bone treated in accordance with the invention, i.e., lyophilizing such bone in the presence of a mechanical strength-conserving agent, will exhibit a level of mechanical strength which is at least 10% greater than that of a comparable specimen of monolithic bone which has been lyophilized in the absence of a mechanical strength-conserving agent.

The term "biocompatible" and expressions of like import shall be understood to mean the absence of stimulation of a severe, long-lived or escalating biological response to an implant and is distinguished from a mild, transient inflammation which accompanies implantation of essentially all foreign objects into a living organism and is also associated with the normal healing response.

DETAILED DESCRIPTION OF THE INVENTION

Bone for implantation is obtained aseptically in a morgue or an operating room from a cadaver donor. The bone is cleansed using 70% ethanol and washed with water for injection and sonication. The bone may be treated with antibiotics such as polymyxin B sulphate, bacitracin, and/or gentamicin, and may contain trace amounts of residual antibiotics. Cleansing, cutting, sizing, shaping, container sterilization, filling, lyophilization, and stoppering functions are performed under conditions following industry standards for tissue handling. The bone employed in the invention is of monolithic proportions in contrast to "particles," "filaments," "threads," "strips," etc., as described in U.S. Pat. Nos. 5,073,373, 5,314,476 and 5,507,813. Thus, the bone treated according to the method of the invention is generally a relatively large piece or segment of donor bone and is intended for implantation into a correspondingly relatively large defect or other implantation site. Typically, the bone herein will possess dimensions of length on the order of about 2 mm to about 500 mm and preferably at least about 5 mm to about 100 mm. Similarly, dimensions of width will be on the order of about 1 mm to about 600 mm and preferably at least about 1 mm to about 100 mm. Dimensions of thickness will be on the order of about 1 mm to about 30 mm and preferably at least about 1 mm to about 10 mm. Such bone can be readily obtained by any one of several methods, including but not limited to, cutting, forming and machining.

Prior to lyophilization, the prepared bone is contacted with a mechanical strength-conserving amount of a biocompatible mechanical strength-conserving agent. The biocompatible mechanical strength-conserving agent appropriate to the invention is a compound or solution that is liquid from about 15° C. to about 45° C., more preferably a liquid at the temperature at which it is contacted with the bone, and which penetrates the small pores of the bone remaining therein after lyophilization. The conserving agent is biocompatible and nontoxic and does not interfere with the normal healing of the graft. A suitable conserving agent will meet these criteria even if mixed with water and then subsequently the water is removed during lyophilization leaving the conserving agent behind, i.e., it has a eutectic point significantly below the freezing point of water. Suggested classes of conserving agent would include polyhydroxy compound, polyhydroxy ester, fatty alcohol, fatty alcohol ester, fatty acid, fatty acid ester, liquid silicone, mixtures thereof, and the like.

Examples of suitable conserving agent include, but are not limited to:

(i) Polyhydroxy compound, for example, glycerol, 1,4,-butylene glycol, diethylene glycol, triethylene glycol, tetraethylene glycol, propylene glycol, dipropylene glycol; polyoxyethylene-polyoxypropylene copolymer, e.g., of the type known and commercially available under the trade names Pluronic and Emkalyx; polyoxyethylene-polyoxypropylene block copolymer, e.g., of the type known and commercially available under the trade name Poloxamer; alkylphenolhydroxypolyoxyethylene, e.g., of the type known and commercially available under the trade name Triton, and the like.

(ii) Polyhydroxy ester, for example, monoacetin, triacetin, poly(oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters; e.g., mono- and tri-lauryl, palmityl, stearyl, and oleyl esters; e.g., of the type available under the trade name Tween from Imperial Chemical Industries; polyoxyethylene fatty acid esters; e.g., polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol; e.g., of the type known and commercially available under the trade name Imwitor; sorbitan fatty acid esters, e.g., of the type known and commercially available under the trade name Span, including sorbitan-monolauryl,-monopalmityl, -monostearyl,-tristearyl, -monooleyl and trioleylesters; monoglycerides, e.g., glycerol mono oleate, glycerol mono palmitate and glycerol monostearate, for example as known and commercially available under the trade names Myvatex, Myvaplex and Myverol, and acetylated, e.g., mono- and di-acetylated monoglycerides, for example as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly(dimethyl siloxane) and polyalkyl arylsiloxane.

As stated above, the suitable biocompatible mechanical strength-conserving agent selected from the examples above preferably is capable of penetrating the small pores of the bone. Therefore, optionally, a solution of a conserving agent can be utilized. This solution can be aqueous or can be one utilizing a polar organic solvent. The biocompatible mechanical strength-conserving agent, neat or solution, should have a viscosity at 20° C. of no greater than about 1410 cps, preferably the viscosity is between about 2 and about 300 cps. The preferred biocompatible mechanical strength-conserving agent is glycerol, more preferably a 50% aqueous solution of glycerol.

The bone is contacted with a mechanical strength-conserving amount of the mechanical strength-conserving agent in a suitable container, e.g., a 120 ml or 500 ml bottle. Optionally, the conserving agent can be applied by infusing, e.g., employing a pressurized system such as that described in U.S. Pat. No. 5,846,484 the contents of which are incorporated herein by reference. Optionally, the conserving agent can be contacted with the bone in the presence of a low pressure atmosphere such as that described in U.S. Pat. No. 5,513,662 the contents of which are incorporated herein by reference. Optionally, the conserving agent can be contacted with the bone in the presence of alternating vacuum and positive pressure such as that provided by the Hypercenter™ XP Enclosed Tissue Processor commercially available from Shandon Lipshaw USA. As one skilled in the art will readily appreciate, the optimal times and levels of alternating vacuum-positive pressure can be determined through routine experimentation.

To assist the mechanical strength-conserving agent in penetrating the small pores of the bone, the bone and agent can be advantageously subjected to sonication. Sonicating bone is well known in the art and is described in U.S. Pat. No. 5,797,871 the contents of which are incorporated herein by reference. After the bone has been in contact with the conserving agent for a period of about 5 minutes to about 7 days, preferably at least about one hour, it is lyophilized following procedures well known in the art. For example, the bottle containing bone and conserving agent is initially frozen to −76° C. with the bone and conserving agent later being subjected to a vacuum of less than 100 militorr while the temperature is maintained at or below −35° C. The end point of the lyophilization procedure is the determination of residual moisture of approximately 5%. Once the bone has been lyophilized, it is stored in sealed, vacuum-contained, bottles prior to its reconstitution and use.

The monolithic bone treated in accordance with the invention, i.e., lyophilizing such bone in the presence of a mechanical strength-conserving agent, will exhibit a level of mechanical strength which is at least about 10%, preferably at least about 20%, and more preferably at least about 30% greater than that of a comparable specimen of monolithic bone which has been lyophilized in the absence of a mechanical strength-conserving agent.

There are a variety of conditions by which lyophilized bone can be rehydrated prior to implantation. Rehydration can be performed by soaking the lyophilized bone in rehydrating solution at normal atmospheric pressure. Alternatively, the lyophilized bone can be rehydrated in a low atmospheric pressure environment, for example, the rehydration solution can be introduced via hypodermic needle through the sealed rubber stopper. The strength-conserving agent also acts as a wetting agent decreasing the time necessary to rehydrate the bone at the time of use.

The rehydration solution can be any of a number of suitable agents such as normal saline, physiologically buffered saline, dextrose solution, antibiotic solutions, and others of this sort. Optionally, it can contain one or more wetting agents or any of a variety of medically/surgically useful substances such as antiviral agents, particularly those effective against HIV and hepatitis; antimicrobials and/or antibiotics such as erythromycin, bacitracin, neomycin, penicillin B, tetracycline, viomycin, chloromycetin and streptomycin, cetazolin, ampicillin, azactam, tobramycin, clindamycin, gentamicin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; antigenic agents; cytoskeletal agents; bone morphogenic proteins (BMPs), transforming growth factor (TGF-beta), insulin-like growth factor (IGF-1); growth hormones such as somatotropin.

The rehydrated lyophilized monolithic bone prepared according to the method herein is intended to be applied at a bone defect site, e.g., one resulting from injury, defect brought about during the course of surgery, infection, malignancy or development malformation. The bone, suitably sized and shaped as required, can be utilized as a graft or replacement in a wide variety of orthopaedic, neurosurgical and oral and maxillofacial surgical procedures such as the repair of simple and compound fractures and nonunions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

The invention will be more fully understood by way of the following example which is intended to illustrate but not limit methods in accordance with the present invention.

EXAMPLE

Bovine cortical bone specimens, 4 mm×4 mm×40 mm (nominal) were prepared from the same bovine femur. Some specimens were soaked in a 50% aqueous solution of glycerol for three days prior to lyophilization. Other specimens were lyophilized without glycerol. After lyophilization, the specimens were tested in 3-point bending (30 mm span, center loaded) in the MTS servo hydraulic testing system. Loading was conducted at a rate of 25 mm/min under displacement control. Specimens were loaded to failure. Data were collected on maximal load, failure load and energy absorbed to break (a measure of how brittle the material is). Factors were compared by the Wilcoxon non-parametric test.

Samples:
Glycerol/Dry n=4
Glycerol/Saline n=2
No glycerol/dry n=3
No glycerol/Saline n=3

|  | Break Load (kN) | Energy to break (N–m) |
| --- | --- | --- |
| Glycerol/Dry | 0.277 ± 0.022 | 0.037 ± 0.0025 |
| Glycerol/Saline | 0.205 ± 0.037 | 0.037 ± 0.0021 |
| No glycerol/Dry | 0.234 ± 0.064 | 0.028 ± 0.0072 |
| No glycerol/Saline | 0152 ± 0.016 | 0.028 ± 0.0135 |

Many of the specimens that were exposed to saline showed a number of fine, internal longitudinal cracks that were visible macroscopically. Both glycerol-treated and non treated specimens displayed this morphology. For all specimens, peak load was equivalent to break load. Glycerol application was a significant factor in determining breaking load (p=0.05), and marginally significant in the energy to breakage (p=0.08). Saline hydration was significant to the breaking load (p=0.03) but not other parameters.

Glycerol application prior to lyophilization reduces brittleness in the bone samples. Freeze-drying, composed of a freezing step and a water-removal step, is damaging to bone and has been shown to negatively affect mechanical properties. Yet, the bone literature teaches that freezing itself is not detrimental to bone to any significant degree. Thus, it is believed that the damage protection offered by the strength-conserving agent does not act by eliminating damage in the freezing, but rather by eliminating damage due to dimensional changes during the drying aspects of freeze-drying. Although the mechanism of the invention is not entirely understood, the inventors believe that this improvement is achieved by maintaining the liquid environment of the bone to reduce damage during lyophilization. Strength was improved by an average of 34% and energy absorption prior to fracture was improved by up to 32%.

What is claimed is:

1. A method for treating monolithic bone intended for implantation to conserve the mechanical strength of the bone during lyophilization and subsequent packaging and maintain such strength during the storage of the bone, the method comprising:

a) contacting the bone with a mechanical strength-conserving amount of at least one biocompatible mechanical strength-conserving agent, said agent being a liquid organic material which is capable of penetrating and remaining in the bone during its lyophilization, packaging and storage;

b) lyophilizing the bone containing the mechanical strength-conserving agent; and, c) packaging the lyophilized bone.

2. The method of claim 1 further comprising infusing under pressure the mechanical strength-conserving agent.

3. The method of claim 1 further comprising sonicating the bone and mechanical strength-conserving agent.

4. The method of claim 1 further comprising contacting the bone and the mechanical strength-conserving agent in the presence of a low pressure atmosphere.

5. The method of claim 1 further comprising contacting the bone and the mechanical strength-conserving agent in the presence of alternating vacuum and positive pressure.

6. The method of claim 1 wherein the strength-conserving agent is selected from the group consisting of polyhydroxy compound, polyhydroxy ester, fatty alcohol, fatty alcohol ester, fatty acid, fatty acid ester, liquid silicone and mixtures thereof.

7. The method of claim 6 wherein the polyhydroxy compound is selected from the group consisting of glycerol, 1,4,-butylene glycol, diethylene glycol, triethylene glycol tetraethylene glycol, propylene glycol, dipropylene glycol; polyoxyethylene-polyoxypropylene copolymer, polyoxyethylene-polyoxypropylene block copolymer, and alkylphenolhydroxypolyoxyethylene.

8. Monolithic bone obtained by the method of claim 7.

9. The method of claim 6 wherein the polyhydroxy ester is selected from the group consisting of monoacetin, triacetin and poly(oxyalkylene) glycol ester.

10. The method of claim 6 wherein the fatty alcohol is selected from the group consisting of caproic alcohol, caprylic alcohol, capric alcohol, undecyl alcohol, lauryl alcohol and tridecanol.

11. The method of claim 6 wherein the fatty alcohol ester is selected from the group consisting of ethyl hexyl palmitate, isodecyl neopentate, octadodecyl benzoate and diethyl hexyl maleate.

12. The method of claim 6 wherein the fatty acid is selected from the group consisting of hexanoic acid, heptanaoic acid, octanoic acid, decanoic acid and undecanoic acid.

13. The method of claim 6 wherein the fatty acid ester is selected from the group consisting of polyoxyethylene-sorbitan-fatty acid ester, polyoxyethylene fatty acid esters, mono-, di-, and mono/di-glycerides, sorbitan fatty acid esters, n-butyl stearate, n-butyl oleate and n-propyl oleate.

14. The method of claim 6 wherein the liquid silicone is selected from the group consisting of polyalkylsiloxane and polyalkylarylsiloxane.

15. The method of claim 14 wherein the polyalkylsiloxane is selected from the group consisting of polymethylsiloxane and poly(dimethylsiloxane).

16. Monolithic bone obtained by the method of claim 6.

17. The method of claim 1 wherein the mechanical strength-conserving agent is glycerol.

18. Monolithic bone obtained by the method of claim 17.

19. The method of claim 1 wherein the mechanical strength-conserving agent is an aqueous solution of glycerol.

20. Monolithic bone obtained by the method of claim 19.

21. The method of claim 1 wherein the mechanical strength-conserving agent is an alcoholic solution of glycerol.

22. Monolithic bone obtained by the method of claim 21.

23. The method of claim 1 further comprising:

d) contacting the lyophilized bone just prior to implantation with a rehydrating amount of at least one rehydration solution to rehydrate the bone.

24. The method of claim 23 wherein the rehydration solution is selected from the group consisting of normal saline, physiologicly buffered saline, dextrose solution, wetting agents, medically/surgically useful substance(s) and antibiotic solutions.

25. Monolithic bone obtained by the method of claim 24.

26. A The method of claim 24 wherein the medically/surgically useful substance(s) is at least one member of the group consisting of bone morphogenic proteins (BMPs), transforming growth factor (TGF-beta) and insulin-like growth factor (IGF-1).

27. Monolithic bone obtained by the method of claim 26.

28. Monolithic bone obtained by the method of claim 23.

29. The bone of claim 28 wherein the strength is at least about 10% greater than that of a comparable specimen of monolithic bone which has been lyophilized in the absence of a mechanical strength-conserving agent.

30. The bone of claim 28 wherein the strength is at least about 30% greater than that of a comparable specimen of monolithic bone which has been lyophilized in the absence of a mechanical strength-conserving agent.

31. The bone of claim 28 wherein the strength is at least about 20% greater than that of a comparable specimen of monolithic bone which has been lyophilized in the absence of a mechanical strength-conserving agent.

32. Monolithic bone obtained by the method of claim 1.

33. A lyophilized monolithic bone implant containing at least one biocompatible mechanical strength-conserving agent, said agent being a liquid organic material which is capable of penetrating and remaining in the bone during its lyophilization, packaging and storage.

34. The monolithic bone of claim 33 wherein the strength-conserving agent is selected from the group consisting of polyhydroxy compound, polyhydroxy ester, fatty alcohol, fatty alcohol ester, fatty acid, fatty acid ester, liquid silicone and mixtures thereof.

35. The monolithic bone of claim 34 wherein the polyhydroxy compound is selected from the group consisting of glycerol, 1,4,-butylene glycol, diethylene glycol, triethylene glycol, tetraethylene glycol, propylene glycol, dipropylene glycol; polyoxyethylene-polyoxypropylene copolymer, polyoxyethylene-polyoxypropylene block copolymer, and alkylphenolhydroxypolyoxyethylene.

36. The monolithic bone of claim 34 wherein the medically/surgically useful substance is at least one member of the group consisting of bone morphogenic proteins (BMPs), transforming growth factor (TGF-beta) and insulin-like growth factor (IGF-1).

37. The monolithic bone of claim 33 wherein the mechanical strength-conserving agent is glycerol.

38. The monolithic bone of claim 33 wherein the mechanical strength-conserving agent is an aqueous solution of glycerol.

39. The monolithic bone of claim 33 wherein the mechanical strength-conserving agent is an alcoholic solution of glycerol.

40. The monolithic bone of claim 33 further comprising at least one medically/surgically useful substance.

* * * * *